Figure 1:
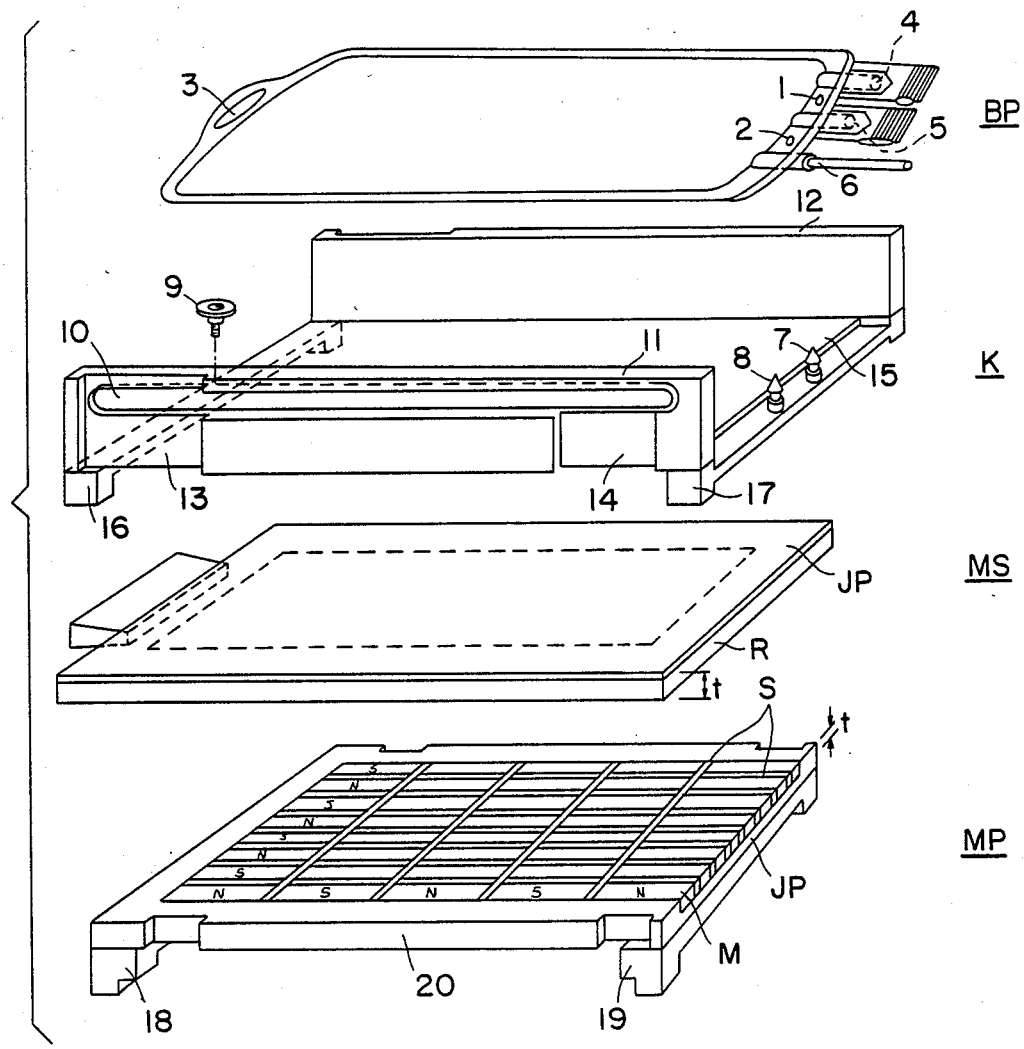

United States Patent [19]

Sorensen et al.

[11] Patent Number: 4,910,148

[45] Date of Patent: Mar. 20, 1990

[54] MAGNETIC SEPARATION OF MAGNETIZED PARTICLES FROM BIOLOGICAL FLUIDS

[75] Inventors: Otto Sørensen; Gunnar Kvalheim, both of Oslo; Eivind Siem, Gjettum, all of Norway

[73] Assignee: Dynal A. S., Oslo, Norway

[21] Appl. No.: 130,912

[22] Filed: Dec. 10, 1987

[30] Foreign Application Priority Data

Feb. 10, 1987 [NO] Norway ................................ 870513
Nov. 11, 1987 [NO] Norway ................................ 874695
Nov. 16, 1987 [NO] Norway ................................ 874770

[51] Int. Cl.$^4$ ..................... C12N 13/00; C12N 5/00; C12M 3/00; B03C 1/00
[52] U.S. Cl. .................................. 435/317.1; 209/213; 210/222; 435/2; 435/173; 435/239; 435/240.1; 435/261; 435/284; 435/286; 435/287; 435/316; 435/803; 436/526; 436/824
[58] Field of Search ............... 210/222; 435/2, 7, 316, 435/173, 239, 240.1, 240.24, 261, 284, 286, 287, 803, 317.1; 436/526, 824; 209/212, 213

[56] References Cited

U.S. PATENT DOCUMENTS 4,624,923 11/1986 Margel ................................. 435/176
4,710,472 12/1987 Saur et al. ........................... 435/287
4,752,563 6/1988 Kortright ............................. 435/4 X Primary Examiner—David M. Naff
Attorney, Agent, or Firm—Seidel, Gonda, Lavorgna & Monaco

[57] ABSTRACT

A method and device are provided for separating magnetized particles from biological fluids. Cells such as cancer cells coated with magnetized particles can be separated from uncoated healthy cells. A fluid mixture of cancer cells, healthy cells and magnetizable particles is introduced into a container such as a disposable blood bag which is attached in a cassette on an underlying plane magnetic plane that provides a magnetic field. Incubation is carried out during which the cancer cells become coated with the magnetizable particles. The magnetic field pulls the coated cells down towards the bottom of the bag and anchors them, and uncoated healthy cells are removed from the bag. The separated uncoated healthy cells may be advanced through a final separation unit where any loose magnetizable particles are removed. There is provided means for adjusting vertical distance between the cassette and the magnetic plane and for agitating fluid within the container attached to the cassette. A magnetic screen plate may be placed between the cassette and the magnetic plate to short circuit the magnetic field during incubation. The screen plate is removed to carry out separation.

14 Claims, 3 Drawing Sheets

BP

MK

MAGNETIC SEPARATION OF MAGNETIZED PARTICLES FROM BIOLOGICAL FLUIDS

The present invention relates to a method and a device for magnetic separation of cells coated with magnetizable particles from uncoated cells in a mixture comprising a carrier, coated, and uncoated cells.

Monoclonal antibodies which are absorbed or chemically connected to monodisperse polymer particles containing iron will bind with the corresponding antigene on the cell membrane of the target cells when added to a cell suspension. By the aid of a magnet the cells which have cells bound to the surface may be extracted from the suspension.

This separation technique may be used for separation of all kinds of cells that are coated with magnetizable particles, i.e. cells which one desires to retain (positive separation), and cells to be removed (negative separation).

The previously known method is based on magnetic liquid flow separation of cells that are coated with magnetizable particles. A disadvantage of this technique is that the particles are readily pulled off the cell surface due to strong turbulence in the liquid flow. Some cells which are coated with particles escape from the magnetic separation field due to the received kinetic energy, especially in case of great velocity of the liquid flow. With moderate velocity, and a large volume of cell suspension the separation will require a relatively long time.

It is an object of the present invention to provide a method of separation of this kind which permits sterile, rapid, efficient, and clean separation of cells, also, in case of a large separation volume, and which is, furthermore, simple and practical in use.

According to the invention this is achieved by a method for magnetic separation of the kind mentioned above that is characterized by the fact that the cell mixture is supplied to a container the volume of which is not completely filled up, and which is subjected to slight movement.

In a further development of the invention a sterile, closed bag, e.g. a disposable blood bag, is used as a container and is fastened in a cassette on an underlying, plane magnetic disk.

According to a further feature a magnetic screen plate is provided between the cassette and the magnetic disc, said magnetic screen plate short circuiting the magnetic field during incubation and then being removed during separation so that the magnetic field can penetrate into the cell suspension to pull cells that are covered with particles, and excess particles down towards the bottom of the bag.

The invention, furthermore, comprises a device for carrying out the above mentioned method, especially for main separation of cancer cells from healthy cells, which device is characterized by comprising a container that may be secured in a cassette that is provided on an underlying, plane magnetic plate by the aid of an adjustable suspension. The device is, in turn, attached to a rockable support.

According to the invention the magnet plate is constructed of small permanent magnets and can, thus, be adapted to the bag-size (volume for separation) that is needed.

In a further development of the device it also comprises a screen plate which may be arranged between said magnet plate and the cassette for short circuiting the magnetic field.

Furthermore, the invention comprises a device for final separation, removal of any loose particles containing iron in the purified cell suspension from the main separation unit. This device is characterized in that the purified cell suspension is pumped through a 150 ml plastic bag (blood bag) which is enclosed in a void having a thickness of 2 mm, between a hinged lid and an underlying plane magnet plate with the edge of a triangular bar that is attached to the underside of the lid pressing the bag together along the centre with the lid in a locked position in order to increase the length of the separation path of the liquid flow.

The method and the device according to the present invention permit sterile rapid efficient and clean separation of cells, also in case of large volumes of liquid. This is achieved by use of disposable plastic bags (blood bags) as containers for the cell suspension and a magnet plate that may be adapted to the bag area.

Since the cell suspension in the main separation unit is not subjected to turbulence of flow, but is by the aid of a tilting table set in slight agitating motion in a closed plastic bag that is not filled up completely, the problems of particles being pulled off from the cell surface and with particles which escape from the magnetic separation field due to their kinetic energy (high flow velocity) are avoided. The device with step-wise adjustable separation velocities permits a moderate acceleration of the particles preventing them from being pulled off the target cells to which tehy are bound, if the magnetic attraction gets too high. A more complete and clean separation is, furthermore, achieved by pumping the purified cell suspension from the main separation, by discharging, through the final separation unit where any loose particles will be caught by the magnetic field.

Utilization of the method for separating tumor cells from bone marrow liquid showed that the invention renders possible an efficient removal of 1 million tumor cells/milliliter bone marrow liquid without hurting the bone marrow cells, and with a purity of approx. 6 log, i.e. 1 tumor cell/$10^6$ normal cells after two purifications. Incubation, separation, discharge, and final separation may be carried out in one and the same set.

Figure 2:
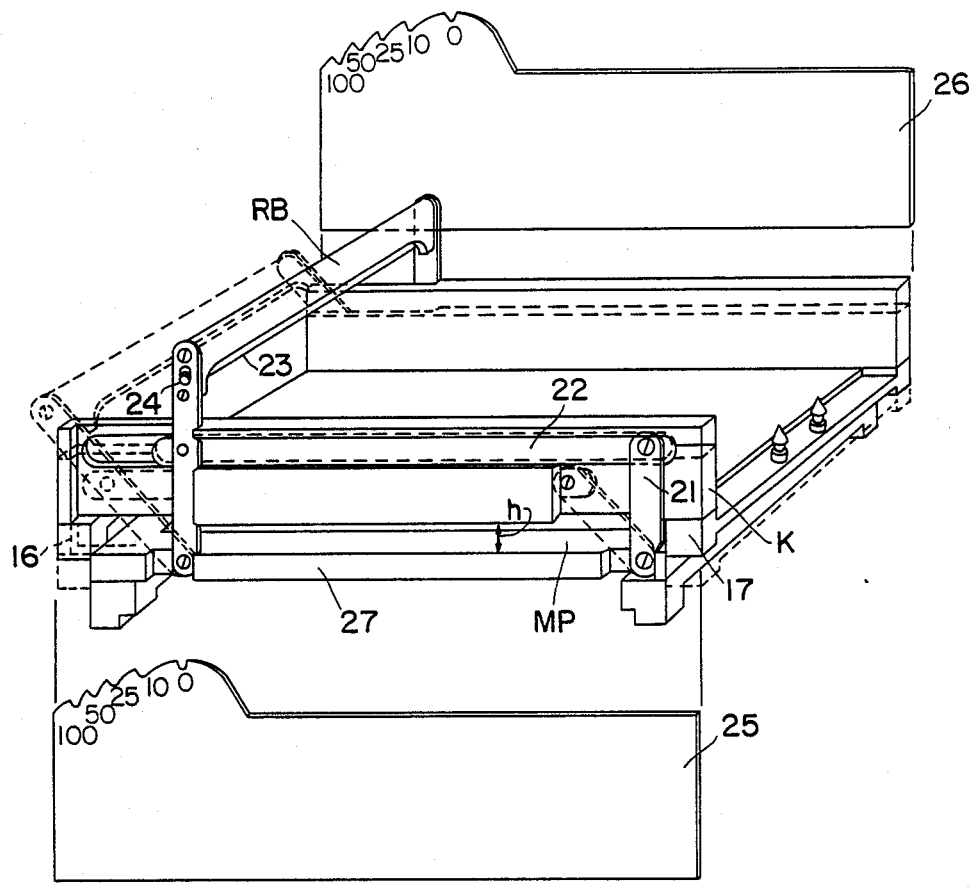
Figure 3A:
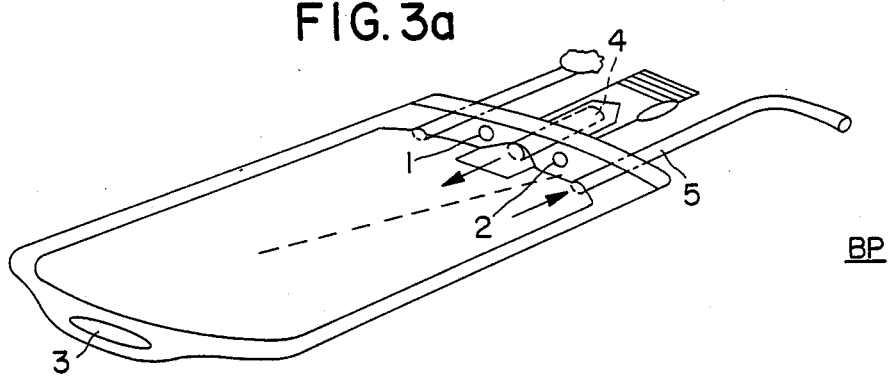

The invention is now to be disclosed in more detail with reference to the drawing, wherein FIG. 1 shows the device for magnetic main separation according to the invention, with the separate parts of the device shown in an exploded view;

FIG. 2 shows an assembly drawing of the device with the adjusting frame (RB) in 0-position (minimal field intensity) in solid lines, and with the frame in a maximum position (maximum field intensity), dotted lines;

FIGS. 3a, b, and c show the magnetic separation cassette for final separation. FIG. 3c is a cross sectional view of the cassette in a locked position.

In the embodiment shown in FIG. 1 the blood bag BP is clamped to cassette K by the aid of fastening orifices 1, 2, and a loop, and corresponding lugs 7, 8, and a button 9. Lugs 7, 8 are mounted on a recessed level to make room for the connecting hoses 4, 5, 6 of the bag for sterile filling and emptying operations. Cassette K, FIG. 2, is linked with magnet plate MP, by the aid of adjusting frame RB, and tie rod 21 which is, in turn, movably connected with a sliding rail 22 made of low frictional plastic material (e.g. "DELRIN"). Sliding roll 22 is placed in a groove 10 in side wall 11 and is slidable along said groove. In the side wall there are, additionally, two recessed levels 13, 14 permitting free movement of adjusting frame and tie rod. A corresponding connection is provided on the opposite side 12 of the cassette (not shown). The bottom 15 of the cassette consists of an anti-magnetic material, e.g. a thin brass sheet. The remaining portions of the cassette may be made of aluminum in order to reduce its weight. The internal distance between guide rails 16, 17, FIGS. 1 and 2, is equal to the length of magnet plate MP. The guide rails serve to keep the cassette in place in relation to the magnet plate. The magnet plate MP is constructed from permanent-magnets M (e.g. samarium-cobalt) having a low profile and high field intensity. The magnets are placed on an iron plate JP. This iron plate functions to enhance the intensity of the gradient magnet field on the upper side of the magnets. The magnets are separated by spacers S, having approximately the same thickness as that t of the magnets, and being oriented in such a manner that each magnet has an adjacent magnet of the opposite polarity. Thus, a maximum extension of the field lines and an advantageous field gradient increasing the area of separation are achieved. The arrangement with the adjusting frame provides for a clean separation due to the fact that the field intensity influencing the magnetizable particles may be adjusted. In this manner the velocity of separation may be determined to prevent particles from being pulled off the cell surface in case of a too high separation. When separation is completed the separated content is anchored when adjusting frame is positioned for maximum field. The iron plate with the magnets is inserted in a base plate 20, so that the upper side of the magnets and the plate are at the same level. Feet 18, 19 serve as supports on an underlying tilting table. The tilting table is in motion during the entire incubation, separation and discharge period to avoid sedimentation and aggregation of cells in the bag.

Magnet screen MS consists of a frame R made of plastic or aluminium and serving as a base for an iron plate JP. The thickness of the screen t is equal to the height h, FIG. 2 when adjusting frame RB is in 0-position (h=max.).

The adjusting frame RB, FIG. 2, is provided with a spring loaded release rail 23 with a locking pin 24 at each end. The locking pins fit into corresponding locking grooves 0, 10, 25, 50, 100 on side plates 25, 26. The side plates are screwed onto the lateral edges 27 of the magnet plates. By depressing the release rail the locking pins are pulled out of locking grooves and the adjusting frame is released and can be adjusted to a desired position. The position of said frame will influence the distance h, FIG. 2, between the bottom of the cassette, and the magnet plate. Distance h determines the intensity of the gradient magnet field from the magnet plate penetrating into the bag through the bottom of the cassette.

By the special structure of the magnet plate comprising permanent magnets separated to a certain distance and with adjacent magnets of opposite polarity high field penetration and an advantageous field gradient are achieved providing for an efficient and large area of separation which is adapted to the bag size (volume of separation) needed.

Figure 3B:
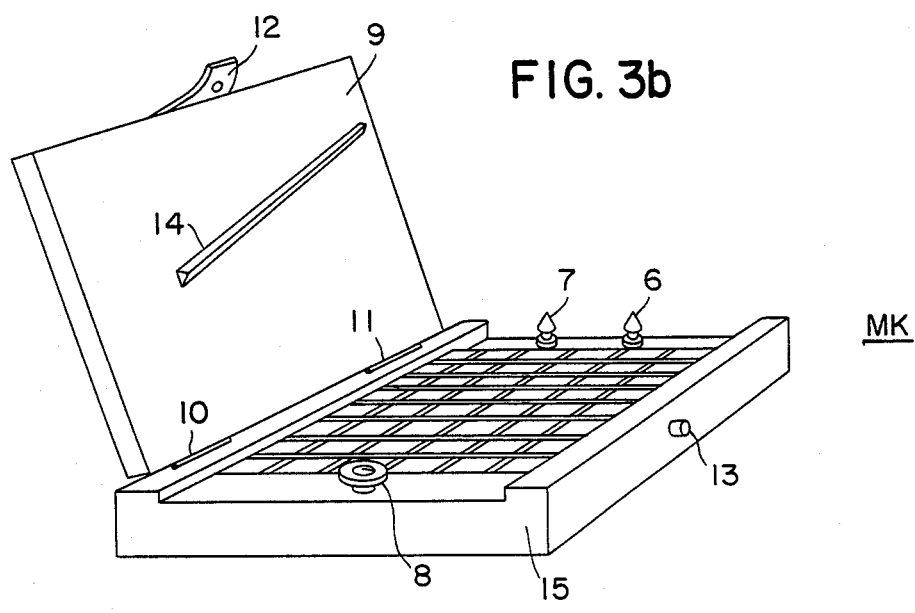
Figure 3C:
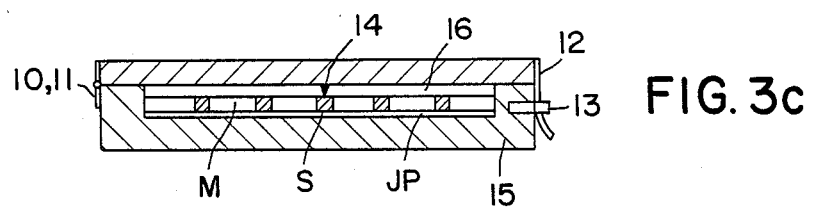

The final separation occurs by use of a blood bag BP, FIG. 3a, which is clamped onto magnet cassette MK, FIG. 3b, by the aid of apertures 1, 2, and loop 3, and corresponding lugs 6, 7, and button 8 on the cassette. The lid 9 with hinges 10, 11 may be locked onto cassette frame 15 by the aid of a snap lock 12, 13. Magnets M, spacers S, and iron plate JP, FIG. 3c are inserted in the cassette frame 15 to provide a void 16 with a thickness of approx. 2.0 mm. With the lid in a locked position the edge of triangular bar 14, which is mounted beneath said lid, press down onto the bag (dotted line, FIG. 3a) across approximately ⅔ of the length of the bag, determined by the length of the bar. Said triangular bar may, e.g. be made from hard plastic or an antimagnetical stainless steel alloy, and the lid may, e.g. be of transparent plastic material.

When the purified cell suspension is discharged it is pumped from the main separation through hose connection 4 to flow in the direction of the arrow along one half of the bag and, furthermore, along the second half of the bag and out of orifice 5 to a collecting bag.

A high degree of purity of the purified cell suspension is achieved by the fact that a strong gradient magnet field extends all over the bag area, and by a long liquid flow path due to the fact that the bag is divided along its center. Any loose particles containing iron will be caught and held back by the magnet field. The fact that the bag is limited to a thin layer (small volume) provides for slight losses of purified cell suspension. Flow turbulences are of no great importance to the final separation since loose particles are to be removed.

Below follows an example of how the present invention may be carried out.

EXAMPLE

A sterile 600 ml blood bag is filled with 400 ml of a liquid suspension comprising unseparated mononuclear bone marrow $1 \times 10^7$ cells/ml) and monodisperse plastic balls containing iron (Ugelstad-balls) with a diameter of 4.5 μm, treated with a monoclonal antigene. Ratio of mixture: 50 balls/antigene-binding cell.

The suspension is incubated for 30 minutes. The cell suspension is put into slight agitating motion by the aid of a tilting table having an adjustable tilting frequency. The tilting table is in motion during the entire separating procedure with an ambient temperature of +4° C. The balls bind to the surface of the target cells (tumor cells) with the corresponding antigenes. Cells and balls keep afloat in the liquid suspension without aggregation or sedimentation. A magnetic screen plate is placed on top of the magnets to prevent the magnet field from penetrating into the bag.

The separation period is 10 minutes. The magnetic screen plate is removed. The magnetic separation field is gradually increasing (10–25–50–100%). The magnetic field pulls all incubated cells (tumor cells) and excess balls down towards the bottom of the bag.

Discharge velocity is 42 ml/min. The precipitated content, tumor cells and excess balls is kept firmly "anchored" to the bottom of the bag by maximum field intensity (100% position). The remaining cell suspension (purified bone marrow) is sucked out of the bag by the aid of a peristaltic pump with adjustable suction velocity, and is advanced through the final separation unit where any loose balls are caught.

The bone marrow liquid is, furthermore, pumped into a storage bag for a second purification step. After finished separation the finally purified bone marrow is transferred into freezing bags, after having been centrifuged and prepared for deep freezing and storage in liquid nitrogen for later thawing and returning to the patient from whom the bone marrow was originally removed. The disposable blood bags with remains are disposed of after each purification.

The loss of separation of 20% after purification twice of totally original normal (healthy) bone marrow cells which are of use for clinical utilization.

We claim:

1. A device for separating magnetized particles from biological fluids in which said magnetized particles are suspended, said device comprising:
   (a) a sample container having an inlet means for introducing biological fluids thereinto and an outlet means for withdrawing biological fluids therefrom,
   (b) a magnetic plate means comprising a plurality of low profile, high field density, permanent magnets, wherein the plurality of magnets are oriented on a generally horizontal base plate such that each magnet is spaced from the others and is adjacent magnets having an opposite polarity,
   (c) a sample cassette means for holding said sample container in a generally vertical position, said sample cassette means being located above, and generally parallel to, said magnetic plate means,
   (d) an adjusting means, operatively connected to said sample cassette means and said magnetic plate means, for adjusting the vertical distance between said sample cassette means and said magnetic plate means, and
   (e) a rocker support means for agitating the fluid contents within said sample container.

2. A device in accordance with claim 1, wherein said sample container comprises a sterile, closed bag.

3. A device in accordance with claim 2, wherein said sample container comprises a disposable blood bag.

4. A device in accordance with claim 1, wherein said base plate comprises a magnetizable material.

5. A device in accordance with claim 4, wherein said base plate comprises iron.

6. A device in accordance with claim 1, wherein said plurality of magnets are spaced from one another with spacers, and wherein said spacers are approximately the same vertical thickness as each magnet.

7. A device in accordance with claim 1, wherein the lower portion of said sample cassette means comprises a generally vertical guide means, slidably mounted to said magnetic plate means, for preventing substantial lateral movement of said sample cassette means and for maintaining said sample cassette means in a generally parallel position directly above said magnetic plate means.

8. A device in accordance with claim 1, wherein said adjusting means comprises:
   (a) an adjusting frame pivotably mounted to said magnetic plate means,
   (b) a tie rod generally parallel to said adjusting frame and pivotably mounted to said magnetic plate means,
   (c) a generally horizontal sliding rail pivotably mounted at its opposite ends to said adjusting frame and said tie rod,
   and wherein said sample cassette means comprises generally vertical side walls each having a guide dimensioned such that said sliding rail can move horizontally therein.

9. A device in accordance with claim 1, wherein said rocker support means comprises a tiltable table which is in direct contact with the lower portion of said magnetic plate means.

10. A device in accordance with claim 1 further comprising a screen plate, said screen plate being slidably mounted between said sample cassette means and said magnetic plate means, and said screen plate being made of a material which substantially blocks the magnetic field, emanating from said magnetic plate means, from reaching the lower surface of said sample cassette means.

11. A method for separating at least a portion of magnetized particles from biological fluids in which magnetized particles are suspended, said method being carried out with a device which comprises: a sample container having an inlet means for introducing biological fluids therein and an outlet means for withdrawing biological fluids therefrom; a magnetic plate means comprising a plurality of low profile, high field density, permanent magnets, wherein the plurality of magnets are oriented on a generally horizontal base plate such that each magnet is spaced from the others and is adjacent magnets having an opposite polarity; a sample cassette means for holding said sample container in a generally vertical position, said sample cassette means being located above and generally parallel to said magnetic plate means; an adjusting means, operatively attached to said sample cassette means and said magnetic plate means, for adjusting the vertical distance between said cassette means and said magnetic plate means; and a rocker support means for agitating the fluid contents within said sample container, said method comprising the steps of:
   (a) partially filling said sample container through said inlet means with a biological fluid in which are suspended magnetized particles,
   (b) attaching said sample container to said sample cassette means,
   (c) adjusting the distance between said sample cassette means and said magnetic plate means with said adjusting means while simultaneously agitating the fluid contents within said sample container with said rocker support means, and
   (d) withdrawing said biological fluid through said sample container outlet means while retaining said magnetized particles by said magnetic plate means with said container.

12. A method in accordance with claim 11, wherein said sample container is partially filled with said biological fluid containing magnetized particles after said sample container is affixed to said sample cassette means.

13. A method in accordance with claim 11, wherein a screen plate is positioned between said sample cassette means and said magnetic plate means prior to partially filling said sample container, said screen plate substantially blocking the transmission of a magnetic field from said magnetic plate means to the fluid contents within said sample container.

14. A method in accordance with claim 13, wherein said screen plate is removed from between said sample cassette means and said magnetic plate means after partially filling said sample container with said biological fluids comprising magnetized particles and after said sample container is affixed to said sample cassette means.

* * * * *